United States Patent [19]

Turano

[11] Patent Number: 4,971,977

[45] Date of Patent: Nov. 20, 1990

[54] ANTI-VIRAL PHARMACEUTICAL COMPOSITIONS

[76] Inventor: Adolfo Turano, 82, Venezia Street, Milan, Italy

[21] Appl. No.: 437,453

[22] Filed: Nov. 15, 1989

Related U.S. Application Data

[63] Continuation of Ser. No. 224,575, Jul. 26, 1988, abandoned.

[30] Foreign Application Priority Data

Jul. 27, 1987 [IT]  Italy .............................. 21457 A/87

[51] Int. Cl.$^5$ ............................................. A61K 31/47
[52] U.S. Cl. .................................................... 514/307
[58] Field of Search ......................................... 514/307

[56] References Cited

PUBLICATIONS

Physicians' Desk Reference, 27ed, 1973, pp. 922, 923 & 1438.
Müller et al., Proc. Natl. Acad. Sci., USA, vol. 79, pp. 1629–1633, Mar., 1982.
Turano et al., Med. Biol. Eur, 4, pp. 861–865 (1976).
Chemical Abstracts 101: 122415p (1984).
Chemical Abstracts 107: 168330j (1987).

Primary Examiner—Jerome D. Goldberg
Attorney, Agent, or Firm—Bucknam and Archer

[57] ABSTRACT

Pharmaceutical compositions containing papaverine inhibit the replication of the HIV or HTLV virus, responsible of the Acquired Deficiency Syndrome (AIDS).

1 Claim, No Drawings

ANTI-VIRAL PHARMACEUTICAL COMPOSITIONS

This is a continuation of U.S. application Ser. No. 224,575, filed July 26, 1988, now abandoned The present invention refers to pharmaceutical compositions useful for the treatment of the Acquired Immuno Deficiency Syndrome (AIDS), containing papaverine as the active ingredient.

AIDS has now become a world-wide epidemic. In the absence of effective therapeutic measures, a continuous expansion of said syndrome has to be expected. To date, the research efforts are aiming both at developing a vaccine and at discovering drugs capable of providing immediate therapeutic responses, which, in some way, may challenge the effects provoked by the aethiologic agent, namely a retrovirus known as HIV or HTLV (Human Immunodeficiency Virus or Human T-lymphocytes Virus).

The most promising drugs presently under investigation such as, for instance, azidothymidine, bis-deoxycytidine, suramine, phosphonoformate, antimony tungstate, are characterized by the common mechanism of action based on the inhibition of the reverse transcriptase (RT), an enzyme necessary for the replication of retroviruses. Unfortunately a severe limitation to the clinical use of such drugs is represented by their high toxicity, which makes desirable the discovery of new agents to be employed in the treatment of this pathology.

We have now surprisingly found that papaverine is capable of effectively inhibiting the replication of the HIV-virus in human lymphocytes through a mechanism which does not involve the inhibition of the enzyme reverse transcriptase; therefore, papaverine, which has been, and continued to be widely employed in the human therapy as a spasmolytic and cerebral vasodilator, can find a useful therapeutic application in the treatment of patients affected by AIDS, thus improving the general conditions and the functionality of the immunitary System, usually severely compromised.

Recently, the in vitro antiviral activity of papaverine against certain viruses was described, as an example type I - herpes virus, adeno - and measles virus, chickenpox-and MSV-Harvey virus, murine retrovirus (Müller et al., Proc. natl. Acad. Sci: 79, 1639–1633, 1982 and Turano et al., Med. Biol. Enr. 4, 861–865, 1976). However, what is known so far on the antiviral activity of papaverine does not make obvious the effectiveness observed in accordance with the present invention in view of the following facts:

(a) the published data only refer to in vitro results, thus they are not sufficiently predictable of the more complex physiologic reality;

(b) it is known that agents active against certain viruses can be totally inactive against other viruses of different species;

(c) notwithstanding the extensive research efforts of the last years, the HIV or HTLV virus proved to be considerably different from any other type of human viruses, and the all classic antiviral agents so far known proved to be ineffective.

According to the hereinbelow reported data, papaverine would display its action through the inhibition of the viral proteins and, consequently, it might be advantageously employed in combination with other agents presently under investigation and endowed with a different mechanism of action, like the inhibitors of the reverse transcriptase. In fact, it can be reasonably foreseen a synergistic effect of two agents having different targets in the replication cycle of the pathogenic virus, with the consequent possibility of increasing the global efficacy of the treatment and decreasing the side-effects through the decrease of the dosages of the single drugs, in particular of the more toxic one. In experiments carried out on H9 cells infected with HIV and exposed for 20 days to scalar dosages of papaverine, repeated at every change of medium, a marked inhibition of the viral replication at a concentration of 10 $\mu$g/ml was observed, a concentration which does not significantly influence the cell proliferation. The presence of HIV in the cultures was determined by means of the RT activity (Cancer Res. 45, 4592, 1985) and the expression of the viral protein p24, measured by radioimmunoassay, as described in the Int. J. Cancer, 38, 587, 1986. In the same type of cells, infected with HIV and exposed for 15 days to 10 $\mu$g/ml of papaverine, the viral proteins were determined by extraction from the cultures at day 5, 10 and 15, and detection through the Western transfer technique.

Already at day 5, a partial reduction of the viral proteins was observed, whereas at day 15 an almost complete disappearance of all the viral bands was noted. On the contrary, cultures not exposed to papaverine, showed a distribution of the proteins typical of that of HIV. Analogous results were obtained by employing infected human lymphocytes; again at a dose of 10 $\mu$g/ml, papaverine was able to reduce the viral infectivity and to challenge the decrease of lymphocytes (PBMC) induced by the virus. Also the viral markers (RT and p24) were significantly reduced, with a reduction of about 40% of the RT activity and a p24 expression 7-times lower than that of the controls.

Also the formation of syncitial cells was considerably reduced (p $\leq$ 0.01) following incubation with papaverine.

A similar effect was observed by employing lymphocytes previously incubated with papaverine and subsequently infected with HIV. In addition it can be assumed that papaverine displays an immunomodulating in vivo effect, co-operating with the above indicated effects.

In view of the above reported data and the negligible toxicity of papaverine (already employed as a medicament in other therapeutic fields since a long time), the present invention deals with pharmaceutical compositions for the treatment of the Acquired Immuno Deficiency Syndrome (AIDS) containing papaverine as the active ingredient.

Said compositions can be administered by oral or parenteral route and prepared in a conventional way by using known methods and excipients, as an example those described in "Remington's Pharmaceutical Sciences Handbook", Hack Pub. Co. N.Y. U.S.A. Typical pharmaceutical compositions may comprise capsules, tablets, syrups, vials for intravenous or intramuscular administration and sustained release preparations.

The compositions may optionally contain other active ingredients displaying useful or complementary activity such as, for instance, azidothymidine, suramine, phosphonoformate, antimony tungstate, bis-deoxycytine, immunomodulators and analogs.

The posology of papaverine depends on several factors, like body weight, sex, patient age, and is generally comprised between about 50 and about 500 mg by dosage unit; it can be administered from 1 to 4 times per day. The treatment can continue for several weeks or months thanks to the low toxicity of the active ingredient and, if necessary, taking advantage of the continuous release technique achieved with the aid of suitable technical means or ligands. Anyway, the best treatment protocols are determined by the art expert on the basis of the observed. clinical parameters.

What is claimed is:

1. The method of treating a patient affected by the acquired immunodeficiency syndrome which consists of administering to said patient papaverine by the oral or parenteral route in the dose of about 50 to 500 mg 1–4 times per day.

* * * * *